(12) United States Patent
Lanier et al.

(10) Patent No.: US 11,360,011 B2
(45) Date of Patent: Jun. 14, 2022

(54) PROCESSES FOR PREDICTING SMALL SCALE STEADY STATE (S4) CRITICAL TEMPERATURES

(71) Applicant: CHEVRON PHILLIPS CHEMICAL COMPANY LP, The Woodlands, TX (US)

(72) Inventors: Elizabeth M. Lanier, Bartlesville, OK (US); Mark J. Lamborn, Bartlesville, OK (US); Brent A. Fiedler, Bartlesville, OK (US); Chung C. Tso, Bartlesville, OK (US); John T. Blagg, Nowata, OK (US); Alan E. Miller, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 470 days.

(21) Appl. No.: 16/142,891

(22) Filed: Sep. 26, 2018

(65) Prior Publication Data
US 2019/0107474 A1 Apr. 11, 2019

Related U.S. Application Data

(60) Provisional application No. 62/570,994, filed on Oct. 11, 2017.

(51) Int. Cl.
| | |
|---|---|
| *G01N 3/60* | (2006.01) |
| *G01K 13/12* | (2006.01) |
| *G01N 3/30* | (2006.01) |
| *G01N 33/44* | (2006.01) |
| *G01N 3/28* | (2006.01) |

(52) U.S. Cl.
CPC ............. *G01N 3/60* (2013.01); *G01K 13/12* (2013.01); *G01N 3/30* (2013.01); *G01N 33/442* (2013.01); *G01N 3/28* (2013.01); *G01N 2203/001* (2013.01); *G01N 2203/0039* (2013.01); *G01N 2203/0098* (2013.01); *G01N 2203/027* (2013.01); *G01N 2203/0224* (2013.01)

(58) Field of Classification Search
CPC ........................................ G01N 3/60
See application file for complete search history.

(56) References Cited

U.S. PATENT DOCUMENTS

| | | | |
|---|---|---|---|
| 6,867,278 | B2 | 3/2005 | McDaniel et al. |
| 6,935,185 | B2 | 8/2005 | Corleto |
| 7,531,602 | B2 | 5/2009 | Hoang et al. |
| 7,696,280 | B2 | 4/2010 | Krishnaswamy et al. |
| 7,829,646 | B2 | 11/2010 | DesLauriers et al. |
| 8,039,556 | B2 | 10/2011 | Krishnaswamy et al. |
| 8,153,043 | B2 | 4/2012 | Krishnaswamy et al. |

(Continued)

OTHER PUBLICATIONS

Piel et al., "Fast Small scale method to predict materials resistance to rapid crack propagation," (2012) Barcelona conference.*

(Continued)

*Primary Examiner* — Hyun D Park
(74) *Attorney, Agent, or Firm* — Eversheds Sutherland (US) LLP (57) ABSTRACT

This disclosure provides methods of predicting the steady state small scale critical temperatures (S4 $T_c$) of polymer resins and pipes therefrom.

37 Claims, 6 Drawing Sheets

(56) References Cited

U.S. PATENT DOCUMENTS

| | | |
|---|---|---|
| 8,771,816 B2 | 7/2014 | DesLauriers et al. |
| 8,772,165 B2 | 7/2014 | Kim et al. |
| 2016/0115264 A1* | 4/2016 | Rohatgi .............. C08L 23/0815 428/36.9 |

OTHER PUBLICATIONS

ASTM F2231-02 (standard test method) (2013).*
Robert Edward Morgan, Ductile-Brittle Transitions in Pipe Grade Polyethylene PhD Thesis, Univ of London (Year: 1994).*
Krishnwamy, Rajendra K., Ashish M. Sukhadin and Mark J. Lamborn. "Is Pent a True Indicator of PE Pipe Slow Crack Growth Resistance?" Bulletin pp. 816-TN, Chevron Phillips Chemical Company LP. Building 94G, Technology Center, Bartlesville, OK 74004. May 2007. pp. 1-7.
Brawn, et al. "The Defense of Rapid Crack Propagation in Polyethylene Pipes on the Plane Stress Fracture Energy of the Resin." Polymer Engineering and Science. vol. 41, No. 7. Jul. 2001. pp. 1140-1145.
BA Design Procedure and Test Method to Prevent Rapid Crack Propagation in Polyethylene Gas Pipe. Gas Research Institute. Jan. 1979-Apr. 1986. pp. 1-19.

\* cited by examiner

PROCESSES FOR PREDICTING SMALL SCALE STEADY STATE (S4) CRITICAL TEMPERATURES

CROSS REFERENCE TO RELATED APPLICATIONS

This application claims priority to U.S. Provisional Patent Application No. 62/570,994, filed on Oct. 11, 2017, which is incorporated herein by reference in its entirety.

TECHNICAL FIELD OF THE INVENTION

This application relates to processes for predicting the performance of polymer compositions at low temperatures, and methods of making polymer compositions and products.

BACKGROUND

Polymer resins are used in a wide variety of products and applications. For example, polymer resins are often used to manufacture pipes for commercial and residential applications. When polymer resins are used to manufacture pipes, the ability of the polymer resin to resist rapid crack propagation at low temperatures is an important property in determining the appropriate conditions where the pipes may be used. For example, even under the most rigorous manufacturing standards and conditions, pipes manufactured from polymer resins will contain unavoidable defects. These defects may include, for example, micro-voids, micro-cracks, and residual stresses. Under certain conditions in use, these manufacturing defects can lead to rapid crack propagation (RCP), and other catastrophic failures in the pipe. For example, pipes manufactured from polymer resins are more susceptible to RCP at low temperatures.

In order to quantify the performance of the pipe under these conditions, a variety of tests may be used. For example, the small scale steady state (S4) critical temperature ($T_c$) may be determined using the International Organization for Standardization (ISO) 13477 test protocol. However, due to the expense and time required to perform the ISO 13477 protocol, other faster, less expensive tests are often used to estimate the S4 critical temperature of a pipe resin. For example, the S4 critical temperature (S4 $T_c$) can be estimated using the room temperature Charpy impact energy (RTCIE) test, or using the Charpy ductile to brittle transition temperature ($T_{db}$), determined using the American Society for Testing and Materials (ASTM) F2231 testing protocol. However, the correlations between the RTCIE, $T_{db}$, and the S4 critical temperature are often quite poor, so that the estimated S4 critical temperature derived from these methods is often quite inaccurate. Particularly in pipe applications which may need to operate under pressurized conditions or at particularly low temperatures, accurately predicting the S4 critical temperature is of the utmost importance to accurately predicting the performance of the pipe in use.

Accordingly, improved methods of estimating the S4 critical temperature of polymer resins and methods of making pipes from the same are needed.

SUMMARY OF THE INVENTION

This summary is provided to introduce various concepts in a simplified form that are further described below in the detailed description. This summary is not intended to identify required or essential features of the claimed subject matter nor is the summary intended to limit the scope of the claimed subject matter.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

In one aspect, a process is provided which includes the steps of: providing a first notched specimen formed of a first polymer composition and a second notched specimen formed of a second polymer composition, wherein the first and second notched specimens have substantially the same original structural dimensions and, when loaded in tension, each of the first and second notched specimens undergoes a brittle fracture; providing a first pipe formed of the first polymer composition and a second pipe formed of the second polymer composition, wherein the first and second pipes have substantially the same original structural dimensions; conducting a modified Charpy test on the first and second notched specimens to determine a ductile-to-brittle transition temperature ($T_{db}$) for each specimen, the modified Charpy test conducted according to ASTM F2231-02 except that the test temperatures are in the range of from about −80° C. to about 40° C. (inclusive) and the original structural dimensions for the modified Charpy test are selected to impart a plane-strain fracture at an impact area of each specimen; conducting a small-scale steady state (S4) test on each of the first and second pipes according to ISO 13477 to determine a critical temperature ($T_c$) for each pipe; and generating a correlation curve between the ductile-to-brittle temperatures ($T_{db}$) and the critical temperatures ($T_c$).

In another aspect, a process for predicting a S4 critical temperature of a pipe is provided, the process including providing a notched test specimen formed of a test polymer composition, wherein the notched test specimen has substantially the same original structural dimensions as the first and second notched specimens and, when loaded in tension, the notched test specimen undergoes a brittle fracture; conducting a modified Charpy test on the notched test specimen to determine a ductile-to-brittle transition temperature ($T_{db}$) for the notched test specimen; calculating a predicted S4 critical temperature ($T_c$) based on the correlation curve described above.

In another aspect, a process for preparing a polyethylene pipe is provided, the process including generating a correlation curve between ductile-to-brittle temperatures ($T_{db}$) and critical temperatures (Tc) according to any of the preceding aspects; providing a test specimen formed of a test polyethylene composition, wherein the test specimen is notched and has substantially the same original structural dimensions as the first and second notched specimens and, when loaded in tension, the test specimen undergoes a brittle fracture; conducting a modified Charpy test on the test specimen to determine a ductile-to-brittle transition temperature ($T_{db}$) for the test specimen; calculating a predicted S4 critical temperature ($T_c$) of a pipe formed of the test polyethylene composition based on the correlation curve; adjusting the test polyethylene composition to obtain a new polyethylene composition having a desired S4 critical temperature ($T_c$) based on the correlation curve; and melting the new polyethylene composition and forming the molten polyethylene composition into pipe.

BRIEF DESCRIPTION OF THE DRAWINGS

The following figures form part of the present specification and are included to further demonstrate certain aspects of the present disclosure. The invention may be better understood by reference to one or more of these figures in combination with the detailed description of specific aspects presented herein.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs, and unless otherwise indicated or the context requires otherwise, these definitions are applicable throughout this disclosure. Further, unless otherwise required by context, singular terms shall include pluralities and plural terms shall include the singular.

If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Unless explicitly stated otherwise in defined circumstances, all percentages, parts, ratios, and like amounts used herein are defined by weight.

Further, in this connection, certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination.

Regarding claim transitional terms or phrases, the transitional term "comprising", which is synonymous with "including", "containing", or "characterized by" is inclusive or open-ended and does not exclude additional, un-recited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a sample consisting essentially of a particular resin can include impurities typically present in a commercially-produced or commercially-available sample of the resin. When a claim includes different features and/or feature classes (for example, a method step, resin features, and/or product features, among other possibilities), the transitional terms comprising, consisting essentially of, and consisting of, apply only to feature class to which is utilized and it is possible to have different transitional terms or phrases utilized with different features within a claim. While compositions and methods are described in terms of "comprising" various components or steps, the compositions and methods can also "consist essentially of" or "consist of" the various components or steps.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

"Optional" or "optionally" means that the subsequently described event or circumstance can or cannot occur, and that the description includes instances where the event or circumstance occurs and instances where it does not.

The terms "configured for use" or "adapted for use" and similar language is used herein to reflect that the particular recited structure or procedure is used in an olefin polymerization system or process as disclosed herein. For example, unless otherwise specified, a particular structure "configured for use" means it is "configured for use in an olefin polymerization reactor system" and therefore is designed, shaped, arranged, constructed, and/or tailored to effect an olefin polymerization, as would have been understood by the skilled person.

As used herein, "DN" means Diameter Nominal, and refers to the nominal pipe diameter in millimeters.

As used herein, "IPS" means Iron Pipe Size, and refers to the nominal pipe diameter in inches.

The term "olefin" is used herein in accordance with the definition specified by IUPAC: acyclic and cyclic hydrocarbons having one or more carbon-carbon double bonds apart from the formal ones in aromatic compounds. The class "olefins" subsumes alkenes and cycloalkenes and the corresponding polyenes. Ethylene, propylene, 1-butene, 2-butene, 1-hexene and the like are non-limiting examples of olefins. The term "alpha olefin" (α-olefin) refers to an olefin that has a double bond between the first and second carbon atom of the longest contiguous chain of carbon atoms. The term "alpha olefin" includes linear and branched alpha olefins unless expressly stated otherwise.

The terms "polyolefin" or "polymer" as used herein means a substance produced by polymerization of one or more olefins, alone or in combination with suitable comonomers, catalysts, or additives. For example, a "polyolefin" or "polymer" as used herein may be produced with a chromium catalyst, a metallocene catalyst, including a dual metallocene catalyst, a Ziegler-Natta catalyst, or combinations thereof. A "polyolefin" or "polymer" as used herein may be produced in a single reactor, or in a plurality of reactors in series or parallel. A "polyolefin" or "polymer" as used herein may be a monomodal or multimodal polymer.

As used herein, "SDR" means Standard Dimension Ratio, and refers to the ratio between the outer diameter of the pipe and the thickness of the pipe wall.

When describing a range of temperatures, standard dimension ratios, and the like, it is the Applicant's intent to disclose every individual number that such a range could reasonably encompass, for example, every individual number that has at least one more significant figure than in the disclosed end points of the range. As an example, when referring to a standard dimension ratio as between 7 and 21, it is intended to disclose that the standard dimension ratio can be 7, 8, 9, 10, 11, 12, 13, 14, 15, 16, 17, 18, 19, 20, or 21, including any subranges or combinations of subranges encompassed in this broader range. Applicant's intent is that these two methods of describing the range are interchangeable. Moreover, when a range of values is disclosed or claimed, Applicant also intends for the disclosure of a range to reflect, and be interchangeable with, disclosing any and all sub-ranges and combinations of sub-ranges encompassed therein. Accordingly, Applicant reserves the right to proviso out or exclude any individual members of any such group, including any sub-ranges or combinations of sub-ranges within the group, or any selection, feature, range, element, or aspect that can be claimed, if for any reason Applicant chooses to claim less than the full measure of the disclosure, for example, to account for a reference that Applicant may be unaware of at the time of the filing of the application. In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, "substantially" means identical, or at least 90%, at least 90%, at least 95%, at least 98% or at least 99% identical. For example, when used to describe the structural relationship between two or more specimens, "substantially the same" means identical in size along each dimension, or at least 90%, at least 95%, at least 98% or at least 99% identical in size along each dimension.

Adjusting a test polymer composition to obtain a new polymer composition may include adjusting the test polymer composition until it is considered to be on target for a particular polymer specification for the new polymer composition. For example, the step of adjusting the test polymer composition may include adjusting the HLMI of the test polymer composition until it is considered to be on target for the HLMI specification of the new polymer composition. For example, in some embodiments, the step of adjusting the test polymer composition may include adjusting the HLMI of the test polymer composition until it is within about 5%, 10%, 15%, 20%, 25%, 30%, 35%, or 40%, or any ranges therebetween, of a target HLMI. In some embodiments, the step of adjusting the test polymer composition may include adjusting the density of the test polymer composition until it is considered to be on target for the density specification of the new polymer composition. For example, in some embodiments, the step of adjusting the test polymer composition may include adjusting the density of the test polymer composition until it is within about 0.1%, 0.2%, 0.3%, 0.4%, 0.5%, 0.6%, 0.7%, 0.8%, 0.9%, or 1% of a target density.

DETAILED DESCRIPTION OF THE INVENTION

In order to quantify the performance of a polymer, particularly polymers which will be used in pipe applications, various testing methods are available. For example, the small scale steady state (S4) critical temperature may be determined using the ISO 13477 test protocol, or the S4 critical temperature (S4 $T_c$) can be estimated using the room temperature Charpy impact energy (RTCIE) test using the ASTM F2231 testing protocol. Specifically, the Charpy ductile to brittle transition temperature ($T_{db}$) has been used to predict the S4 $T_c$ of polymer resins. However, the correlations between the $T_{db}$ determined using the ASTM F2231 protocol and the S4 $T_c$ are often quite poor.

RTCIE testing generally measures the fracture toughness of a material, to determine the amount of stress required to propagate a preexisting flaw. Generally, the fracture toughness of specimens which have standard proportions but are different thicknesses tend to have different fracture toughness values. However, once the sample thickness exceeds a critical dimension, the value of the fracture toughness becomes relatively constant, and can be expressed as a value $K_{IC}$, which may be considered the plane-strain fracture toughness. RTCIE testing generally involves loading a sample in tension, where a notched sample may be placed on two end supports, and may be subjected to an impact load in its center, causing the sample to bend and fracture.

Without intending to be bound by theory, it is believed that the standard RTCIE test method is a poor predictor of S4 $T_c$ because these samples experience plane stress conditions when impacted. As detailed in the ASTM F2231-02 testing protocol, standard Charpy specimens are 3 mm (+/−0.2 mm) thick, 80 mm (+/−1 mm) long, and 10 mm (+/−0.2 mm) deep, with a 2.5 mm (+/−0.02 mm) notch centered within a distance of 40 mm (+/−0.5 mm) from each end. Accordingly, the thickness of standard Charpy specimens is substantially smaller than the length or depth of the standard Charpy specimens. When the sample is impacted during testing, it is believed that the normal stress $\sigma_z$, acting in the specimen through-thickness direction, and shear stresses, $\sigma_{xz}$, and $\sigma_{yz}$, are assumed to be zero. In other words, when the sample is impacted during testing, it is believed that these samples experience plane stress conditions. Typically, plane stress occurs when the geometry of the body is essentially planar, with one dimension being much smaller than the others, such as the very small thickness of standard Charpy specimens as compared to their length and depth. Under these conditions, it is believed that the measured $T_{db}$ values will depend on both the resin used for the test, and the specific geometry of the test sample. Because $T_{db}$ values will, in part, depend on the particular geometry of the sample, their correlation with the S4 $T_c$ will be inaccurate.

Without intending to be bound by theory, it is believed that, by adjusting the size of the specimen used in the ASTM F2231-02, the conditions can be adjusted so that the sample will experience plane strain conditions when impacted, such that the measured fracture toughness will be at a constant value $K_{IC}$, where it may be considered a material property. In other words, it is believed that, by adjusting the size of the specimen used in standard testing methods, the $T_{db}$ value derived from these methods will depend only on the resin, and not on the sample geometry. Specifically, by adjusting the dimensions of the test sample, it is believed that, when the sample is impacted during testing, the strain normal to the x-y plane, $\varepsilon_z$ and the shear strain $\gamma_{xz}$ and $\gamma_{yz}$ are zero. Because the $T_{db}$ values will not depend on the particular geometry of the sample, it is believed that their correlation with the S4 $T_c$ of the resin will be substantially more accurate than what is achievable with currently available methods In some embodiments, a process is provided which includes providing a first notched specimen formed of a first polymer composition and a second notched specimen formed of a second polymer composition, wherein the first and second notched specimens have substantially the same original structural dimensions.

Next, a first pipe formed of the first polymer composition and a second pipe formed of the second polymer composition may be provided, which each have substantially the same structural dimensions.

In some embodiments, the process further includes conducting a modified Charpy test on the first and second notched specimens to determine a ductile-to-brittle transition temperature ($T_{db}$) for each specimen. In some embodiments, the modified Charpy test is conducted according to ASTM F2231-02 except that the test temperatures are in the range of from about −80° C. to about 40° C. and the original structural dimensions for the modified Charpy test are selected to impart a plane-strain fracture at an impact area of each specimen.

In some embodiments, determining the ductile-to-brittle transition temperature ($T_{db}$) for each specimen includes conducting a modified Charpy test at a plurality of temperatures in the range from about −80° C. to about 40° C., plotting the Charpy energy density (CED) against temperature (T), and conducting a best fit of the dependent variable, CED, as a function of the independent variable, T, using a mathematical function exhibiting only a single inflection point. In some embodiments, this mathematical function is a linear combination of three separate expressions consisting of: (1) a constant, (2) a mathematical function that is equal to zero for $T<T_{db}$ and equal to a first order function of temperature for $T \geq T_{db}$ or greater, and (3) an error function of the product of the temperature difference, $(T-T_{db})$, with a constant. In some embodiments, the inflection point corresponds to the ductile-to-brittle transition temperature ($T_{db}$).

In some embodiments, the process further includes conducting a small-scale steady state (S4) test on each of the first and second pipes according to ISO 13477 to determine a critical temperature ($T_c$) for each pipe.

In some embodiments, the process further includes generating a correlation curve between the $T_{db}$ and $T_c$ which were determined as described above. In some embodiments, the correlation curve may be a linear best fit between the $T_{db}$ and $T_c$. In some embodiments, the correlation curve has a coefficient of determination ($R^2$) which is greater than the comparative coefficient of determination ($R_c^2$) of a comparative calibration curve between $T_{db}$ determined by a standard Charpy test according to ASTM F2231-02 and the critical temperature determined by the standard S4 test according to ISO 13477. In some embodiments, the coefficient of determination ($R^2$) may be at least 5%, 10%, 15%, 20%, 25%, 30%, 35%, 40%, 45%, 50%, 55%, or 60% greater than the comparative coefficient of determination ($R_c^2$)

In some embodiments, the process further includes providing a third notched specimen formed of a third polymer composition and having substantially the same original structural dimensions as the first and second notched specimens and, when loaded in tension, the third notched specimen undergoes a brittle fracture.

Next, a third pipe formed of the third polymer composition may be provided, having substantially the same original structural dimensions as the first and second pipes, as described above.

In some embodiments, the process further includes conducting a modified Charpy test on the third notched specimens to determine a ductile-to-brittle transition temperature ($T_{db}$) for the third specimen. In some embodiments, the modified Charpy test is conducted according to ASTM F2231-02 except that the test temperatures are in the range of from about −80° C. to about 40° C. and the original structural dimensions for the modified Charpy test are selected to impart a plane-strain fracture at an impact area of each specimen. In some embodiments, the process further includes conducting a small-scale steady state (S4) test on each of the first and second pipes according to ISO 13477 to determine a critical temperature ($T_c$) for each pipe.

In some embodiments, the process further includes generating a correlation curve between the $T_{db}$ and S4 $T_c$ which were determined as described above. In some embodiments, the correlation curve may be a linear best fit between the $T_{db}$ and S4 $T_c$.

In some embodiments, a process for predicting a S4 critical temperature of a pipe is provided, including providing a notched test specimen formed of a test polymer composition and, when loaded in tension, the notched test specimen undergoes a brittle fracture. In some embodiments, the notched test specimen has substantially the same original structural dimensions as the first and second notched specimens. In some embodiments, the notched test specimen has substantially the same original structural dimensions as the first, second, and third notched specimens.

In some embodiments, the process for predicting a S4 critical temperature of a pipe further includes conducting a modified Charpy test on the notched test specimen to determine a ductile-to-brittle transition temperature ($T_{db}$) for the notched test specimen, and calculating a predicted S4 critical temperature based on the correlation curve described above. In some embodiments, the step of calculating a predicted S4 critical temperature includes the step of developing an equation to model the correlation curve and calculating the S4 critical temperature based on the measured $T_{db}$ value in that equation.

In some embodiments, the notched specimens each have a thickness defined by:

$$B \geq 2.5 * \left(\frac{K_{IC}}{\sigma_y}\right)^2$$

where B(m) is the thickness of the notched specimen, $K_{IC}(Pa \cdot m^{1/2})$ is the fracture toughness of the notched specimen, and $\sigma_y(Pa \cdot m^{-1})$ is the yield stress of the notched specimen.

In some embodiments, the notched specimens may be substantially the same size in two or more structural dimensions. For example, in some embodiments, the thickness and depth of each specimen may the same. In some embodiments, the length of each sample is about 80 mm, the depth of each sample is about 10 mm, and the thickness of each sample is about 10 mm. In some embodiments, the length of each sample is about 80 mm, the depth of each sample is about 10 mm, and the thickness of each sample is about 20 mm. The dimensions may be selected so that each of the first and second notched specimens undergoes a brittle fracture.

In some embodiments, the ductile-to-brittle transition temperature ($T_{db}$) for each of the notched specimens may be from about −80° C. to about 5° C., for example, about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., and any ranges therebetween.

In some embodiments, each of the notched specimens may be derived from a sample coupon from molded end use articles. For example, each of the notched specimens may be derived from a sample taken from molded polymer end use articles such as extruded pipes, molded fittings, and the like. In some embodiments, each of the notched specimens may be derived from polymer fluff or pellets. In some embodiments, the notched specimens may be formed from a compression molded plaque of the first, second, third, or test polymer composition, respectively. In some embodiments, the compression molded plaque may be formed by heating the first, second, third, or test polymer composition and repeatedly applying and removing pressure. In some embodiments, the compression molded plaque may substantially free of voids. In some embodiments, the compression molded plaque may be at room temperature and ambient pressure.

In some embodiments, the first, second, third, and test polymer composition may comprise a polyethylene resin. For example, the polymer composition may comprise a high density polyethylene resin (HDPE), a medium density polyethylene resin (MDPE) or a low density polyethylene resin (LDPE). In some embodiments, each of the polymer compositions may comprise a bimodal resin. In some embodiments, each of the polymer compositions may comprise one or more copolymers.

In some embodiments, the first pipe, second pipe, third pipe, and test pipe may have a standard dimension ratio (SDR) of from about 7 to about 21, for example, about 7, about 8, about 9, about 10, about 11, about 12, about 13, about 14, about 15, about 16, about 17, about 18, about 19, about 20, or about 21. In some embodiments, the pipe may have a nominal outer diameter of from about 1 to about 20, for example about 1, about 2, about 3, about 4, about 5, about 6, about 7, about 8, about 9, about 10, about 11 about 12, about 13, about 14, about 15, about 16, about 17, about 18, about 19, about 20, or about 21. In some embodiments, the first pipe and the second pipe may be a thermoplastic pipe.

In some embodiments, a process for preparing a polyethylene pipe is provided. In some embodiments, this process includes generating a correlation curve between ductile-to-brittle temperatures ($T_{db}$) as described above, and providing a test specimen formed of a test polyethylene composition. The test specimen is notched and has substantially the same original structural dimensions as the first and second notched specimens and, when loaded in tension, undergoes a brittle fracture. The process may further include conducting a modified Charpy test on the test specimen to determine a ductile-to-brittle transition temperature ($T_{db}$) for the test specimen, and calculating a predicted S4 $T_c$ of a pipe formed of the test polyethylene composition based on the correlation curve, as described above. This process may further include adjusting the test polyethylene composition to obtain a new polyethylene composition having a desired S4 $T_c$ based on the correlation curve. For example, if the calculated S4 $T_c$ is higher than desired, the polymer composition may be adjusted by adding a polymer of a known lower S4 $T_c$ value, to form a new polyethylene composition. For example, in some embodiments adjusting the test polyethylene composition may include altering the percentage of comonomer in the test polyethylene composition, altering the polydispersity index of the test polyethylene composition, altering the molecular weight distribution of the test polyethylene composition, altering the identity of the comonomers used in the test polyethylene composition, altering the relative proportion of constituent polymers in the test polyethylene composition when it is multimodal, or any combination of these alterations. In some embodiments, adjustments may be made repeatedly or incrementally until the new polyethylene composition reaches a desired S4 $T_c$. In some embodiments, the new polyethylene composition is a multimodal medium-density polyethylene or a bimodal polyethylene. In some embodiments, the new polyethylene composition has a density of from about 0.925 g/ml to about 0.942 g/ml, for example about 0.925 g/ml, about 0.93 g/ml, about 0.935 g/ml, about 0.94 g/ml, about 0.942 g/ml, or any ranges therebetween.

In some embodiments, the new polyethylene composition has a Pennsylvania Notch Test (PENT) value of from about 500 hours to about 20,000 hours, for example about 500 hours, about 1000 hours, about 1500 hours, about 2000 hours, about 2500 hours, about 3000 hours, about 3500 hours, about 4000 hours, about 4500 hours, about 5000 hours, about 5500 hours, about 6000 hours, about 6500 hours, about 7000 hours, about 7500 hours, about 8000 hours, about 8500 hours, about 9000 hours, about 9500 hours, about 10,000 hours, about 10,500 hours, about 11,000 hours, about 11,500 hours, about 12,000 hours, about 12,500 hours, about 13,000 hours, about 13,500 hours, about 14,000 hours, about 14,500 hours, about 15,000 hours, about 15,500 hours, about 16,000 hours, about 16,500 hours, about 17,000 hours, about 17,500 hours, about 18,000 hours, about 18,500 hours, about 19,000 hours, about 19,500 hours, about 20,000 hours, or any ranges therebetween. The PENT value is a measurement of the slow crack growth resistance of polyethylene resins and is determined by the ASTM F1473 standard.

In some embodiments, the new polyethylene composition has a Charpy impact energy of from about 1.0 J to about 3.0 J, for example about 1.0 J, about 1.5 J, about 2.0 J, about 2.5 J, about 3.0 J, and any ranges therebetween. In some embodiments, the new polyethylene composition has a flexural modulus, 2% secant of from about 80 kpsi (551.6 MPa) to about 110 kpsi (758.4 MPa), for example about 80 kpsi (551.6 MPa), about 90 kpsi (620.5 MPa), about 100 kpsi (689.5 MPa), about 110 kpsi (758.4 MPa), and any ranges therebetween. In some embodiments, the new polyethylene composition has an elongation at break of greater than about 450%. In some embodiments, the new polyethylene composition has a Young's modulus of from about 120 kpsi (827.4 MPa) to about 190 kpsi (1310.0 MPa). In some embodiments, the new polyethylene composition has a tensile strength at yield of from about 2600 psi (17.9 MPa) to less than about 3,000 psi (20.7 MPa), for example about 2,600 psi (17.9 MPa), about 2,700 psi (18.6 MPa), about 2,800 psi (19.3 MPa), about 2,900 psi (20.0 MPa), about 3,000 psi (20.7 MPa), or any ranges therebetween.

In some embodiments, adjusting the test polyethylene composition may include preparing PE-100 ethylene copolymers using a catalyst system comprising a chromium source or an aluminophosphate support, as described in U.S. Pat. No. 7,829,646, entitled "Olefin polymers, method of making, and use thereof," which is hereby incorporated by reference in its entirety. In some embodiments, adjusting the test polyethylene composition may include preparing bimodal polyethylene resins in which the high molecular weight ethylene copolymer component typically has a relatively narrow molecular weight distribution, with short chain branching content being substantially across its molecular weight distribution, as is described in U.S. Pat. No. 7,696,280, entitled "HDPE resins for use in pressure pipe and related applications," which is hereby incorporated herein in its entirety. In some embodiments, adjusting the polyethylene test composition may include preparing polymers by contacting at least one mono-1-olefin having from 2 to about 20 carbon atoms per molecule and at least one mono-1-olefin co-monomer having from 2 to about 10 carbon atoms per molecule in a reaction zone under polymerization conditions in the presence of a hydrocarbon diluent, a catalyst system, and a co-catalyst, as described in U.S. Pat. No. 6,867,278, entitled "Olefin polymers, method of making, and use thereof," which is hereby incorporated by reference in its entirety.

In some embodiments, adjusting the test polyethylene composition may include adding zinc oxide to a polymer composition, as described in U.S. Pat. No. 8,772,165, entitled "Polyethylene additive compositions and articles made from same", which is hereby incorporated herein by reference in its entirety. In some embodiments, adjusting the polyethylene composition may include adjusting bimodal polyethylene resin properties in which the high molecular weight ethylene copolymer component has a relatively narrow molecular weight distribution, with short chain branching content being substantially constant across its molecular weight distribution, as described in U.S. Pat. No. 8,153,043, entitled "HDPE resins for use in pressure pipe and related applications," which is hereby incorporated herein by reference in its entirety, and as described in U.S. Pat. No. 8,039,556, entitled "HDPE resins for use in pressure pipe and related applications," which is hereby incorporated herein by reference in its entirety.

The new polyethylene composition may be melted and formed into a pipe. For example, the new polyethylene composition may be extruded into a pipe, or molded by conventional means into a pipe shape.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Example 1

Charpy test samples were prepared using a commercially available high density polyethylene (HDPE) polymer pellets, referred to as HDPE(A) (available from Chevron Phillips Chemical Company LP, The Woodlands, Tex., USA). Each sample had a width of 10 mm and a notch depth of 2.5 mm. The samples tested had nine different thicknesses, shown in Table 1.

TABLE 1

| Size No. | Thickness |
|---|---|
| 1 | 2.53 |
| 2 | 4.41 |
| 3 | 6.16 |
| 4 | 8.19 |
| 5 | 10.11 |
| 6 | 12.46 |
| 7 | 14.19 |
| 8 | 17.63 |
| 9 | 22.09 |

Figure 1:
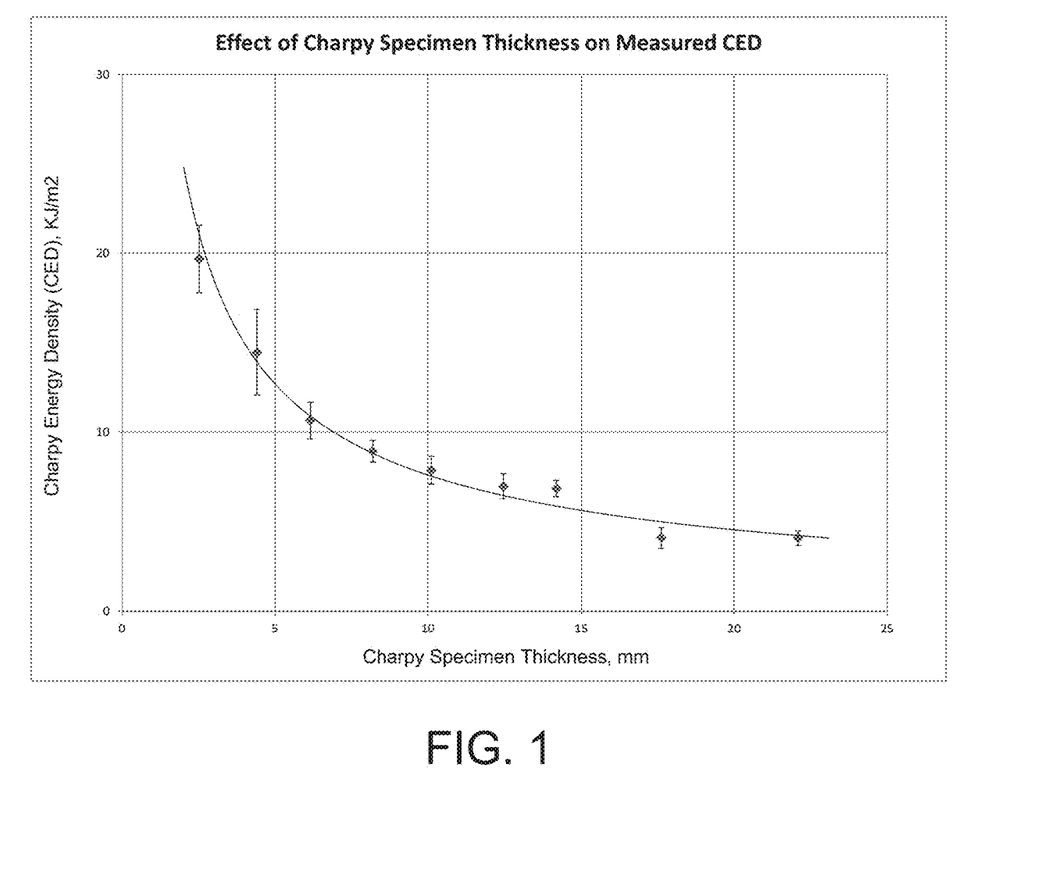
FIG. 1 is a correlation plot of the Charpy energy density measurements obtained from samples made from a high density polyethylene of thicknesses from about 3 mm to about 23 mm with best fit lines.

Five samples of each dimension were prepared and tested, and the Charpy energy density was calculated for each of the five samples. The average Charpy energy density and error bars representing a single standard deviation are shown with a best fit in FIG. 1. As can be seen from this figure, the Charpy energy density of this polymer appears to decrease asymptotically as Charpy specimen thickness increases. While not intending to be bound by theory, it is believed that, as specimen thickness increases, the decrease in Charpy energy density as Charpy specimen thickness increases represents the transition from plane stress to plain strain.

Example 2

Figure 2:
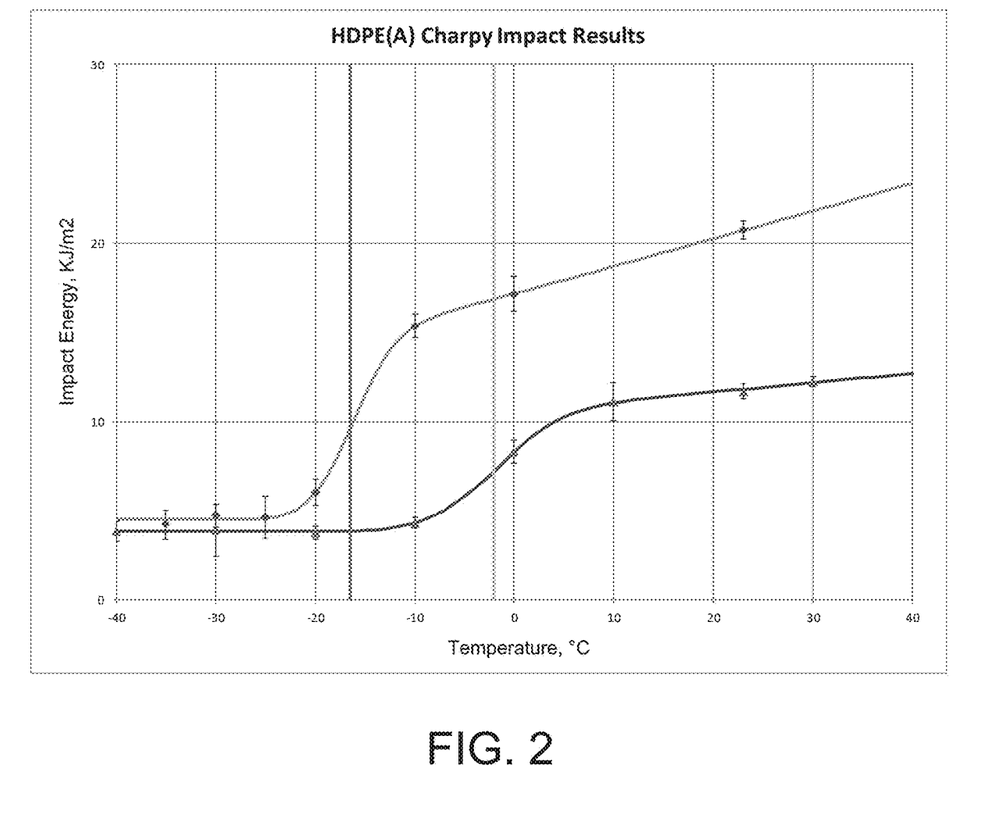
FIG. 2 is a correlation plot of the Charpy energy density measurements obtained from samples made from a high density polyethylene of 3 mm and 10 mm thicknesses over a range of temperatures from about −40° C. to about 40° C. with best fit lines.

First, 2" IPS (DN 50 mm) SDR 11 pipe samples and 8" IPS (DN 200 mm) SDR 11 pipe samples were prepared from the resins identified in Table 2 below. Table 2 below shows the typical known values of S4 $T_c$ for medium density polyethylene pellets, referred to as MDPE (available from Chevron Phillips Chemical Company LP, The Woodlands, Tex., USA) and high density polyethylene polymer pellets (available from Chevron Phillips Chemical Company LP, The Woodlands, Tex., USA). Pipe samples made from Experimental Resin A and Experimental Resin B, which were both metallocene medium density polyethylene (mMDPE) resins, were tested to determine their small scale steady state critical temperature (S4 $T_c$) according to ISO 13477. Standard 3 mm thick Charpy samples were prepared and tested according to ASTM F2231-02, and the Charpy ductile-to-brittle transition temperature ($T_{db}$) was recorded. Next, samples of each resin were prepared for Charpy testing. Each sample was 80 mm long, 10 mm deep, and 10 mm thick, and was then subjected to standard Charpy testing as described in ASTM F2231-02, except that the Charpy impact energy was measured across a range of temperatures from −40° C. to 40° C. and the Charpy ductile-to-brittle transition temperature ($T_{db}$) was recorded. For example, the Charpy energy density results at various temperatures and linear best fits for 3 mm by 10 mm and 10 mm by 10 mm samples of HDPE(A) resins are shown in FIG. 2. The inflection point of each of the linear best fits correlates to the $T_{db}$ determined from both of these sample geometries, and illustrates the difference in $T_{db}$ determined from different sample geometries. The measured Charpy energy density for the 3 mm thick samples are shown in gray diamonds and the measured Charpy energy density for the 10 mm thick samples are shown in gray triangles. Each data point has error bars representing one standard deviation from the measurement at each temperature. The vertical dark gray line represents the calculated $T_{db}$ of the 3 mm thick samples, and light gray vertical line represents the calculated $T_{db}$ of the 10 mm thick samples.

The S4 $T_c$ and Charpy ductile-to-brittle transition temperature ($T_{db}$) results are shown in Table 2:

TABLE 2

$T_{db}$ and S4 $T_c$

| Resin | 3 mm Charpy $T_{db}$ (° C.) | 10 mm Charpy $T_{db}$ (° C.) | 2" IPS SDR 11 S4 $T_C$ (° C.) | 8" IPS SDR 11 S4 $T_C$ (° C.) |
|---|---|---|---|---|
| MDPE Resin | −7.5 | −1.8 | 8 | 22 |
| HDPE(A) Resin | −16.5 | −2.1 | — | 15 |
| Experimental Resin A (mMDPE) | −12.8 | −6.7 | −9.5 | — |
| Experimental Resin B (mMDPE) | −7.8 | −8.6 | −10 | — |

As can be seen from Table 2, the standard Charpy test using a 3 mm thick sample indicates that the HDPE(A) resin has the lowest $T_{db}$, followed by Experimental Resin A, then Experimental Resin B, and then the MDPE resin. However, this does not precisely correlate with the measured or known S4 $T_c$ values of these resins. For example, looking at the 2" IPS SDR 11 S4 $T_c$ values and the 8" IPS SDR 11 S4 $T_c$ values, it is clear that the Experimental Resin B has the lowest S4 $T_c$, followed by the Experimental Resin A, followed by the HDPE(A) resin, and finally followed by the MDPE resin. For clarity, the relative $T_{db}$ and $T_c$ values of these resins are ranked in Table 3, where the resin having the lowest $T_{db}$ or $T_c$ value of those tested is ranked 1 and the resin having the highest $T_{db}$ or $T_c$ value of those tested is ranked 4.

TABLE 3

Relative ranking of $T_{db}$ and S4 $T_c$

| Resin | 3 mm Charpy $T_{db}$ (° C.) | 10 mm Charpy $T_{db}$ (° C.) | 2" IPS SDR 11 S4 $T_C$ (° C.) | 8" IPS SDR 11 S4 $T_C$ (° C.) |
|---|---|---|---|---|
| MDPE Resin | 4 | 4 | 4 | 4 |
| HDPE(A) Resin | 1 | 3 | — | 3 |
| Experimental Resin A (mMDPE) | 2 | 2 | 2 | — |
| Experimental Resin B (mMDPE) | 3 | 1 | 1 | — |

As can be seen from Tables 2 and 3, the $T_{db}$ values determined from Charpy testing with 10 mm thick samples arrived at the proper relative ranking of $T_{db}$ temperatures as compared to known S4 $T_c$ temperatures. That is, the relative values of $T_{db}$ from the 10 mm Charpy sample testing more closely correlate with the known S4 $T_c$ values of these resins.

Example 3

Figure 3:
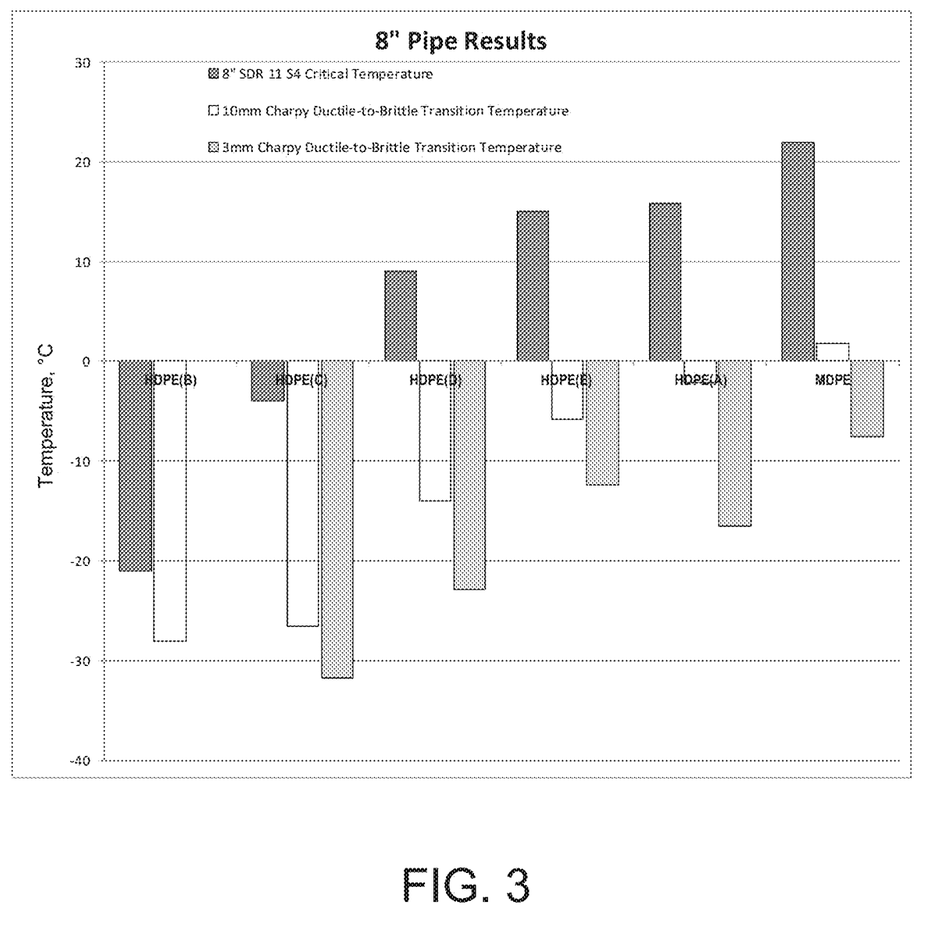
FIG. 3 is a bar graph comparing the Charpy $T_{db}$ results for 3 mm and 10 mm thick Charpy specimens to S4 $T_c$ results for 8" IPS SDR 11 pipe fabricated from various resins. See Example 3.

First, eight inch (8") IPS SDR 11 pipe samples were extruded from high density polyethylene pellets, referred to as HDPE(B) (previously available from Chevron Phillips Chemical Company LP, The Woodlands, Tex., USA) four different types of high density polyethylene pellets, referred to as HDPE(A), HDPE(C), HPDE(D) and HDPE(E) (available from Chevron Phillips Chemical Company LP, The Woodlands, Tex., USA), and medium density polyethylene pellets, referred to as MDPE (available from Chevron Phillips Chemical Company LP, The Woodlands, Tex., USA). These pipe samples were then tested according to ISO 13477 to determine their S4 critical temperatures (S4 $T_c$). The S4 critical temperature for each resin is shown in FIG. 3. As can be seen from FIG. 3, the HDPE(B) resin exhibited the lowest S4 $T_c$, with increasing S4 $T_c$ in each of the HPDE(C), HPDE(D), HPDE(E), HPDE(A), and MDPE resins.

Next, standard 3 mm thick Charpy samples were prepared and tested according to ASTM F2231-02, and the Charpy ductile-to-brittle transition temperature ($T_{db}$) was recorded. These results are shown in FIG. 3 in gray, for all resins other than HDPE(B) resin, because the Charpy results for the 3 mm thick specimens did not exhibit a definite $T_{db}$. As can be seen from this graph, the $T_{db}$ differs significantly from the measured S4 $T_c$ for each resin. Moreover, the $T_{db}$ values measured using a standard 3 mm Charpy sample do not correlate with the measured S4 $T_c$. Specifically, as discussed above, the measured $T_c$ for each resin sample increased steadily moving from left to right across the graph, so that the measured S4 $T_c$ of the HDPE(E) resin was lower than the measured S4 $T_c$ of the HDPE(A) resin. In contrast, the measured $T_{db}$ of the 3 mm Charpy sample of the HDPE(E) resin was higher than the measured $T_{db}$ of the HDPE(A) resin.

Next, Charpy samples were prepared according to ASTM F2231-02, except that the prepared samples were 10 mm thick, rather than 3 mm thick, and the Charpy ductile-to-brittle transition temperature ($T_{db}$) was recorded. These results are shown in FIG. 3. As can be seen from this graph, the $T_{db}$ measured from the 10 mm thick samples differs significantly from the measured S4 $T_c$ for each resin. However, unlike the $T_{db}$ values recorded from standard 3 mm Charpy test samples, the $T_{db}$ values recorded from 10 mm samples correlate extremely well with the S4 $T_c$ values. For example, both the measured S4 $T_c$ and the $T_{db}$ from the 10 mm thick samples increase steadily moving from left to right across the graph, so that the $T_{db}$ of the HDPE(B) resin was lower than the HDPE(C) resin, which was lower than the HDPE(D) resin, and so on.

Figure 4:
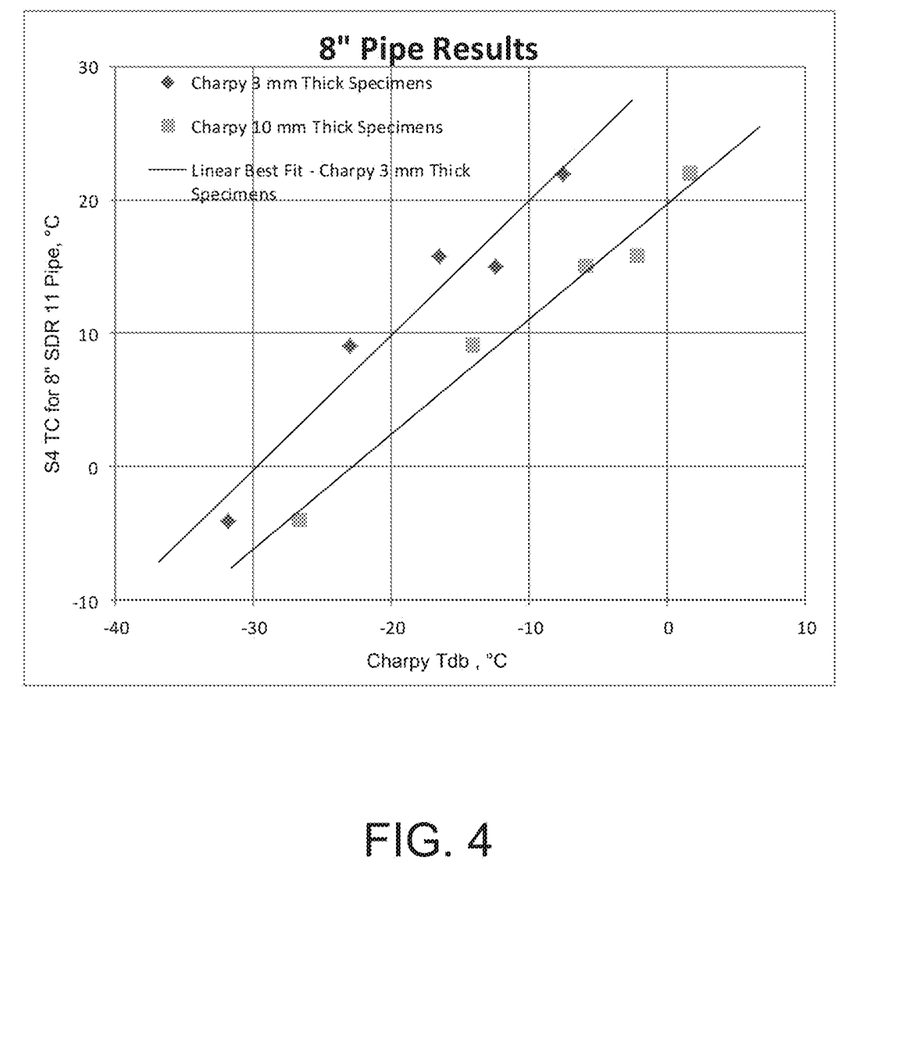
FIG. 4 is a correlation plot of the Charpy results of FIG. 3, with linear best fit lines.

To more precisely measure the correlation between Charpy test results and measured S4 $T_c$ values, linear best fits were prepared, and are shown in FIG. 4. As can be seen from FIG. 4, the linear best fit between the $T_{db}$ values recorded from the Charpy testing of the 3 mm samples and the measured S4 $T_c$ value for 8" IPS SDR 11 pipe has an equation of y=1.01x+30, wherein y is the S4 $T_c$ temperature, and x is the Charpy $T_{db}$ temperature. The coefficient of determination of this best fit ($R^2$) is 0.946. In comparison, the linear best fit between the $T_{db}$ values recorded from the Charpy testing of the 10 mm samples and the measured S4 $T_c$ value for 8" IPS SDR 11 pipe has an equation of y=8.864x+19.7, wherein y is the S4 $T_c$ temperature, and x is the Charpy $T_{db}$ temperature. The coefficient of determination of this best fit ($R^2$) is 0.980, which is significantly higher than the coefficient of determination obtained when using standard 3 mm thick Charpy samples. In other words, testing of 10 mm Charpy samples according to an embodiment of the present disclosure provides a much more accurate prediction of S4 $T_c$ temperature than testing of standard 3 mm Charpy samples.

Example 4

Figure 5:
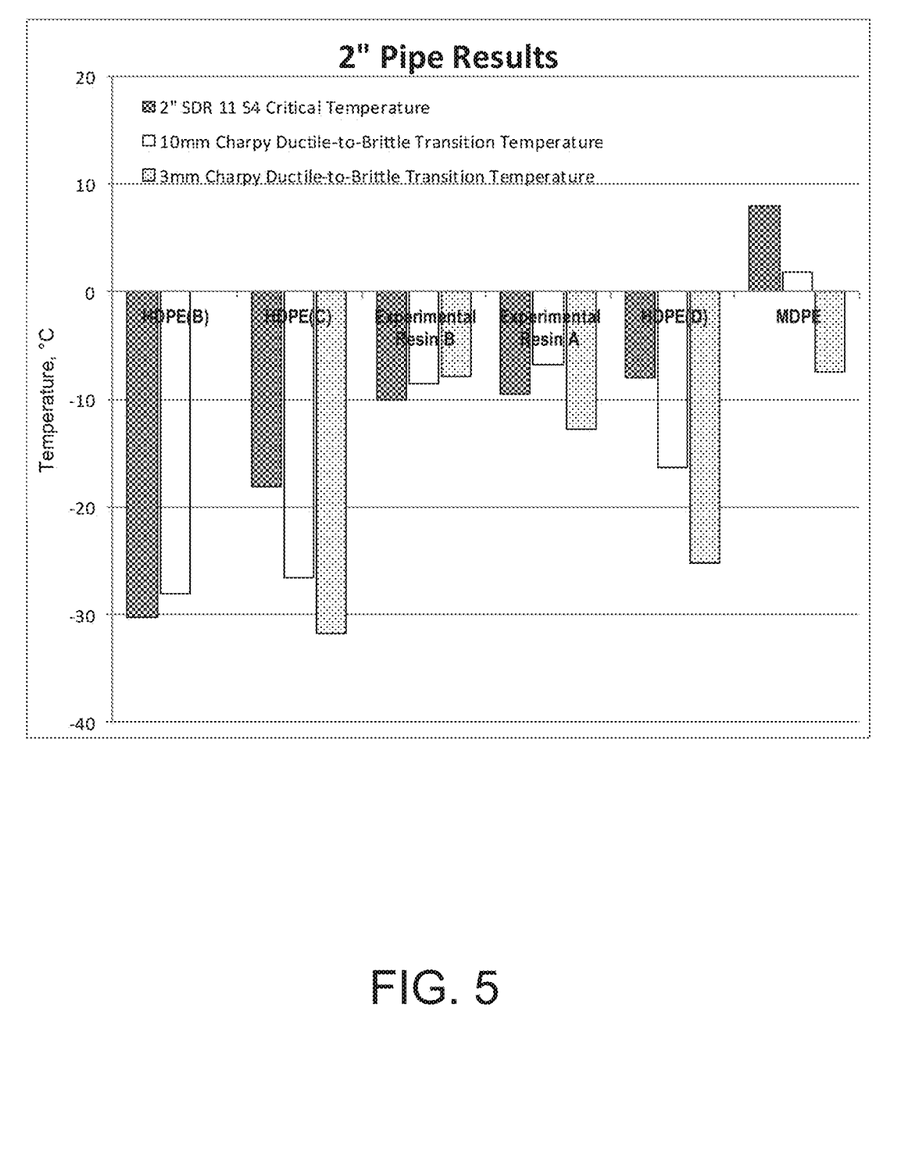
FIG. 5 is a bar graph comparing the Charpy $T_{db}$ results for 3 mm and 10 mm thick Charpy specimens to S4 $T_c$ results for 2" IPS SDR 11 pipe fabricated from various resins. See Example 4.

First, two inch (2") IPS SDR 11 pipe samples were extruded from HDPE(B) pellets (previously available from Chevron Phillips Chemical Company LP, The Woodlands, Tex., USA), HDPE(C) pellets (available from Chevron Phillips Chemical Company LP, The Woodlands, Tex., USA), Experimental Resin A, Experimental Resin B, HDPE (D) pellets (available from Chevron Phillips Chemical Company LP, The Woodlands, Tex., USA), and MDPE pellets (available from Chevron Phillips Chemical Company LP, The Woodlands, Tex., USA). These pipe samples were then tested according to ISO 13477 to determine their S4 critical temperatures (S4 $T_c$). The S4 critical temperature for each resin is shown in FIG. 5. As can be seen from FIG. 5, the HDPE(B) resin exhibited the lowest S4 $T_c$, with increasing S4 $T_c$ in each of the HDPE(C), Experimental Resin B, Experimental Resin A, HDPE(C), and MDPE resins.

Next, standard 3 mm thick Charpy samples were prepared and tested according to ASTM F2231-02, and the Charpy ductile-to-brittle transition temperature ($T_{db}$) was recorded. These results are shown in FIG. 5 in gray, for all resins other than HDPE(B), because the Charpy results for the 3 mm thick specimens did not exhibit a definite $T_{db}$. As can be seen from this graph, the $T_{db}$ differs significantly from the measured S4 $T_c$ for each resin. Moreover, the $T_{db}$ values measured using a standard 3 mm Charpy sample do not correlate well with the measured S4 $T_c$. Specifically, as discussed above, the measured $T_c$ for each resin sample increased steadily moving from left to right across the graph, so that the measured S4 $T_c$ of Experimental Resin B was lower than the measured S4 $T_c$ of Experimental Resin A. In contrast, the measured $T_{db}$ of the 3 mm Charpy sample of Experimental Resin B was higher than the measured $T_{db}$ of Experimental Resin A.

Next, Charpy samples were prepared according to ASTM F2231-02, except that the prepared samples were 10 mm thick, rather than 3 mm thick, and the Charpy ductile-to-brittle transition temperature ($T_{db}$) was recorded according to ASTM F2231-02, except that the test temperatures are in the range of from about −80° C. to about 40° C. These results are shown in FIG. 5. As can be seen from this graph, the $T_{db}$ measured from the 10 mm thick samples differs significantly from the measured S4 $T_c$ for each resin. However, unlike the $T_{db}$ values recorded from standard 3 mm Charpy test samples, the $T_{db}$ values recorded from 10 mm samples correlate extremely well with the S4 $T_c$ values. For example, both the measured S4 $T_c$ and the $T_{db}$ from the 10 mm thick samples increase steadily moving from left to right across the graph other than a single anomaly with the HDPE(D) resin, so that the $T_{db}$ of the HDPE(B) resin was lower than the HDPE(C) resin, which was lower than Experimental Resin B, and so on.

Figure 6:
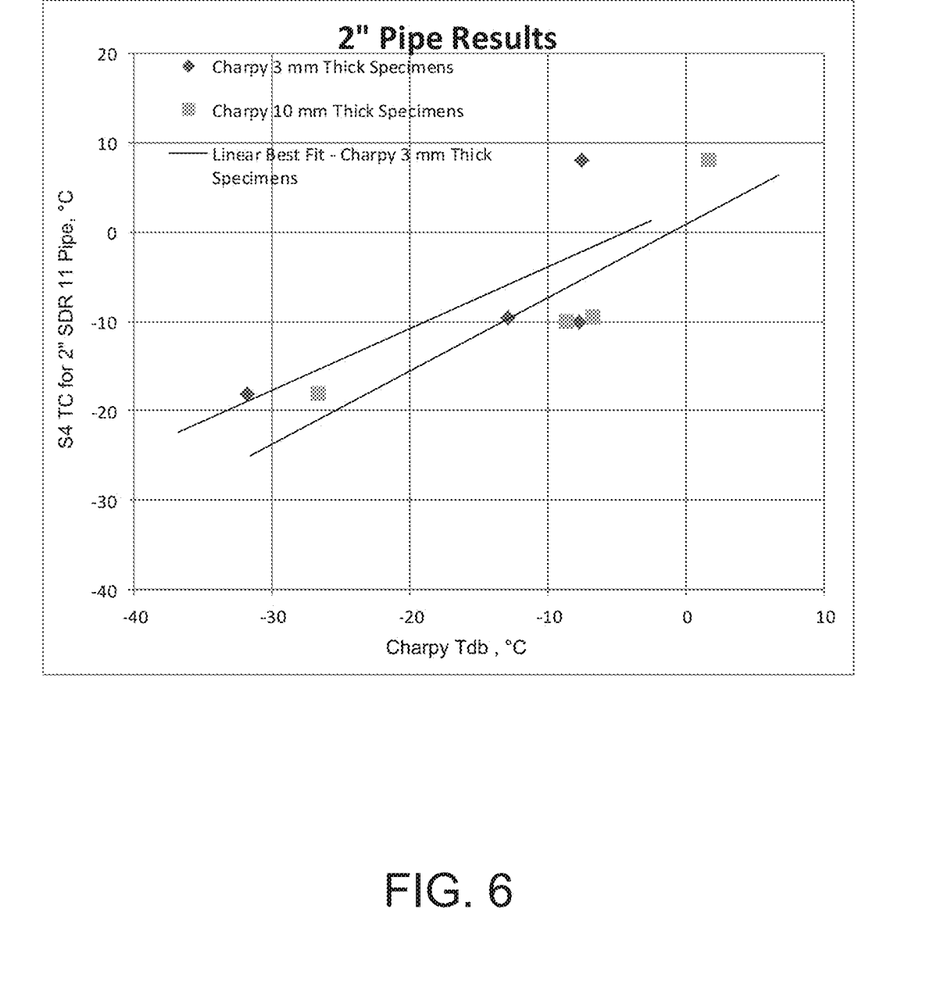
FIG. 6 is a correlation plot of the Charpy results of FIG. 5, with linear best fit lines.

To more precisely measure the correlation between Charpy test results and measured S4 $T_c$ values, linear best fits were prepared, and are shown in FIG. 6. As can be seen from FIG. 6, the linear best fit between the $T_{db}$ values recorded from the Charpy testing of the 3 mm samples and the measured S4 $T_c$ value for 2" IPS SDR 11 pipe has an equation of y=0.689x+2.917, wherein y is the S4 $T_c$ temperature, and x is the Charpy $T_{db}$ temperature. The coefficient of determination of this best fit ($R^2$) is only 0.516, indicating that this is a very poor linear fit of the data. In comparison, the linear best fit between the $T_{db}$ values recorded from the Charpy testing of the 10 mm samples and the measured S4 $T_c$ value for 2" IPS SDR 11 pipe has an equation of y=0.8159x+0.7775, wherein y is the S4 $T_c$ temperature, and x is the Charpy $T_{db}$ temperature. The coefficient of determination of this best fit ($R^2$) is 0.7833— over fifty percent higher than the coefficient of determination obtained when using standard 3 mm thick Charpy samples. In other words, testing of 10 mm Charpy samples according to an embodiment of the present disclosure provides a much more accurate prediction of S4 $T_c$ temperature than testing of standard 3 mm Charpy samples.

Embodiments

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments typically are described as "comprising" but, alternatively, can "consist essentially of" or "consist of" unless specifically stated otherwise)

1. A process comprising:
   providing a first notched specimen formed of a first polymer composition and a second notched specimen formed of a second polymer composition, wherein the first and second notched specimens have substantially the same original structural dimensions and, when loaded in tension, each of the first and second notched specimens undergoes a brittle fracture;

providing a first pipe formed of the first polymer composition and a second pipe formed of the second polymer composition, wherein the first and second pipes have substantially the same original structural dimensions;

conducting a modified Charpy test on the first and second notched specimens to determine a ductile-to-brittle transition temperature ($T_{db}$) for each specimen, the modified Charpy test conducted according to ASTM F2231-02 except that the Charpy test is conducted at temperatures are in the range of from about −80° C. to about 40° C. and except that the original structural dimensions for the modified Charpy test are selected to impart a plane-strain fracture at an impact area of each specimen;

conducting a small-scale steady state (S4) test on each of the first and second pipes according to ISO 13477 to determine a critical temperature ($T_c$) for each pipe; and generating a correlation curve between the ductile-to-brittle temperatures ($T_{db}$) and the critical temperatures ($T_c$).

2. The process according to embodiment 1, wherein providing the first notched specimen comprises:
forming the first notched specimen from a compression molded plaque of the first polymer composition.

3. The process according to any of the preceding embodiments, wherein providing the second notched specimen comprises:
forming the second notched specimen from a compression molded plaque of the second polymer composition.

4. The process according to any of the preceding embodiments, wherein providing the first pipe comprises:
forming the first pipe according to U.S. Pat. No. 8,772,165, 8,153,043 8,039,556, 7,829,646, 7,696,280, or 6,867,278.

5. The process according to any of the preceding embodiments, wherein providing the second pipe comprises:
forming the second pipe according to U.S. Pat. No. 8,772,165, 8,153,043 8,039,556, 7,829,646, 7,696,280, or 6,867,278.

6. The process according to any of the preceding embodiments, further comprising:
providing a third notched specimen formed of a third polymer composition and having substantially the same original structural dimensions as the first and second notched specimens and, when loaded in tension, the third notched specimen undergoes a brittle fracture;
providing a third pipe formed of the third polymer composition and having substantially the same original structural dimensions as the first and second pipes;
conducting the modified Charpy test on the third notched specimen to determine a ductile-to-brittle transition temperature ($T_{db}$) for the third notched specimen;
conducting the S4 test on the third pipe according to ISO 13477 to determine a critical temperature ($T_c$) for the third pipe; and
generating a correlation curve between the ductile-to-brittle temperatures ($T_{db}$) of all the notched specimens and the critical temperatures ($T_c$) of all the pipes.

7. The process according to any of the preceding embodiments, wherein providing the third notched specimen comprises:
forming the third notched specimen from a compression molded plaque of the third polymer composition.

8. The process according to any of the preceding embodiments, wherein providing the third pipe comprises:
forming the third pipe according to U.S. Pat. No. 8,772,165, 8,153,043 8,039,556, 7,829,646, 7,696,280, or 6,867,278.

9. A process for predicting a S4 critical temperature of a pipe, the process comprising:
providing a notched test specimen formed of a test polymer composition, wherein the notched test specimen has substantially the same original structural dimensions as the first and second notched specimens and, when loaded in tension, the notched test specimen undergoes a brittle fracture;
conducting a modified Charpy test on the notched test specimen to determine a ductile-to-brittle transition temperature ($T_{db}$) for the notched test specimen;
calculating a predicted S4 critical temperature ($T_c$) based on the correlation curve according to any one of the preceding embodiments.

10. The process according to embodiment 9, wherein providing the notched test specimen comprises:
forming the notched test specimen from a compression molded plaque of the test polymer composition.

11. The process according to any of the preceding embodiments, wherein the first, second, and third notched specimens and the notched test specimen each has a thickness defined by:

$$B \geq 2.5 * \left(\frac{K_{IC}}{\sigma_y}\right)^2$$

wherein:
B(m) is the thickness of the notched specimen
$K_{IC}$(Pa·m$^{1/2}$) is the fracture toughness of the notched specimen; and
$\sigma_y$(Pa·m$^{-1}$) is the yield stress of the notched specimen.

12. The process according to any of the preceding embodiments, wherein the first, second, and third notched specimens and the notched test specimen each has a thickness from 3 mm to 20 mm.

13. The process according to any of the preceding embodiments, the first, second, and third notched specimens and the notched test specimen each has a thickness from 3 mm to 10 mm.

14. The process according to any of the preceding embodiments, wherein the first, second and third pipes each has a standard dimension ratio of about 7 to about 21.

15. The process according to any of the preceding embodiments, wherein the first, second and third pipes each has a standard dimension ratio of about 9 to about 17.

16. The process according to any of the preceding embodiments, wherein the first, second and third pipes each has a standard dimension ratio of about 11.

17. The process according to any of the preceding embodiments, wherein the first, second and third pipes each has a nominal outer diameter of about 2 to about 16.

18. The process according to any of the preceding embodiments, wherein the first, second and third pipes each has a nominal outer diameter of about 2 to about 8.

19. The process according to any of the preceding embodiments, wherein the ductile-to-brittle transition temperature ($T_{db}$) for each of the first, second and third notched specimens is from about −80° C. to about −5° C.

20. The process according to any of the preceding embodiments, wherein the ductile-to-brittle transition temperature ($T_{db}$) for each of the first, second and third notched specimens is from about −40° C. to about 5° C.

21. The process according to any of the preceding embodiments, wherein the ductile-to-brittle transition temperature ($T_{db}$) for each of the first, second and third notched specimens is from about −25° C. to about 0° C.

22. The process according to any of the preceding embodiments, wherein the S4 $T_c$ for each of the first, second and third pipes is from about −40° C. to about 25° C.

23. The process according to any of the preceding embodiments, wherein the S4 $T_c$ for each of the first, second and third pipes is from about 0° C. to about 20° C.

24. The process according to any of the preceding embodiments, wherein the first, second, and third polymer compositions and the test polymer composition each comprises a polyethylene resin.

25. The process according to any of the preceding embodiments, wherein the first, second, and third polymer compositions and the test polymer composition each comprises a medium-density or a high-density polyethylene.

26. The process according to any of the preceding embodiments, wherein the first, second, and third pipes are each a thermoplastic pipe.

27. The process according to any of the preceding embodiments, wherein the first, second, and third polymer compositions and the test polymer composition each is derived from a sample coupon from molded end use articles, polymer fluff, or pellets.

28. The process according to any of the preceding embodiments, wherein the correlation curve or the revised correlation curve has a coefficient of determination ($R^2$) that is greater than a comparative coefficient of determination ($R_C^2$) of a comparative correlation curve between ductile-to-brittle temperatures determined by a standard Charpy test according to ASTM F2231-02 and the critical temperatures determined by the standard S4 test according to ISO 13477.

29. The process according to embodiment 28, wherein the coefficient of determination ($R^2$) is from about 4% to about 52% greater than the comparative coefficient of determination ($R_C^2$).

30. A process for preparing a polyethylene pipe, the process comprising:
    generating a correlation curve between ductile-to-brittle temperatures ($T_{db}$) and critical temperatures ($T_c$) according to any of the preceding embodiments;
    providing a test specimen formed of a test polyethylene composition, wherein the test specimen is notched and has substantially the same original structural dimensions as the first and second notched specimens and, when loaded in tension, the test specimen undergoes a brittle fracture;
    conducting a modified Charpy test on the test specimen to determine a ductile-to-brittle transition temperature ($T_{db}$) for the test specimen;
    calculating a predicted S4 critical temperature ($T_c$) of a pipe formed of the test polyethylene composition based on the correlation curve;
    adjusting the test polyethylene composition to obtain a new polyethylene composition having a desired S4 critical temperature ($T_c$) based on the correlation curve; and
    melting the new polyethylene composition and forming the molten polyethylene composition into pipe.

31. A process for preparing a polyethylene pipe according to embodiment 30, wherein adjusting the test polyethylene composition comprises or is selected from altering [1] the percentage comonomer in the test polyethylene composition, [2] the polydispersity index of the test polyethylene composition, [3] the molecular weight distribution of the test polyethylene composition, [4] the identity of the comonomer(s) in the test polyethylene composition, [5] the relative proportion of constituent polymers in the test polyethylene composition when it is multimodal, and [6] any combination thereof.

32. A process for preparing a polyethylene pipe according to embodiment 30 or 31, wherein the new polyethylene composition is a multimodal medium-density polyethylene has a density of from about 0.925 g/ml to about 0.942 g/ml.

33. A process for preparing a polyethylene pipe according to any of embodiments 30-32, wherein the new polyethylene composition is a multimodal medium-density polyethylene has a density of from about 0.928 g/ml to about 0.940 g/ml.

34. A process for preparing a polyethylene pipe according to any of embodiments 30-32, wherein the new polyethylene composition is a bimodal polyethylene.

35. A process for preparing a polyethylene pipe according to any of embodiments 30-34, wherein the new polyethylene composition has a PENT value of from about 500 hours to about 20,000 hours as measured by ASTM F1473.

36. A process for preparing a polyethylene pipe according to any of embodiments 30-35, wherein the new polyethylene composition has a Charpy impact energy of from about 1.0 J to about 3.0 J.

37. A process for preparing a polyethylene pipe according to any of embodiments 30-36, wherein the new polyethylene composition has a flexural modulus, 2% secant of from about 80 kpsi to about 110 kpsi.

38. A process for preparing a polyethylene pipe according to any of embodiments 30-37, wherein the new polyethylene composition has an elongation at break of greater than about 450%.

39. A process for preparing a polyethylene pipe according to any of embodiments 30-38, wherein the new polyethylene composition has a Young's modulus of from about 120 kpsi to about 190 kpsi.

40. A process for preparing a polyethylene pipe according to any of embodiments 30-39, wherein the new polyethylene composition has a tensile strength at yield of from about 2600 psi to less than about 3,000 psi.

41. A pipe made according to the process of any of embodiments 30-40.

We claim:

1. A process comprising:
    providing a first notched specimen formed of a first polymer composition and a second notched specimen formed of a second polymer composition, wherein the first and second notched specimens have original structural dimensions which are substantially equal and, when loaded in tension, each of the first and second notched specimens undergoes a brittle fracture;
    providing a first pipe formed of the first polymer composition and a second pipe formed of the second polymer composition, wherein the first and second pipes have original structural dimensions which are substantially equal;
    conducting a modified Charpy test on the first and second notched specimens to determine a ductile-to-brittle transition temperature ($T_{db}$) for each specimen, the modified Charpy test conducted according to ASTM F2231-02 except that the Charpy test is conducted at temperatures are in the range of from about −80° C. to about 40° C. and the original structural dimensions for the modified Charpy test are selected to impart a plane-strain fracture at an impact area of each specimen;

conducting a small-scale steady state (S4) test on each of the first and second pipes according to ISO 13477 to determine a critical temperature ($T_c$) for each pipe; and generating a correlation curve between the ductile-to-brittle temperatures ($T_{db}$) and the critical temperatures ($T_c$), wherein the first and second notched specimens each has a thickness of greater than 4 mm, and wherein the correlation curve has a coefficient of determination ($R^2$) that is greater than a comparative coefficient of determination ($R_C^2$) of a comparative correlation curve between ductile-to-brittle temperatures determined by a standard Charpy test according to ASTM F2231-02 and the critical temperatures determined by the standard S4 test according to ISO 13477.

2. The process according to claim 1, wherein providing the first notched specimen comprises:
forming the first notched specimen from a compression molded plaque of the first polymer composition.

3. The process according to claim 1, wherein providing the second notched specimen comprises:
forming the second notched specimen from a compression molded plaque of the second polymer composition.

4. The process according to claim 1, further comprising:
providing a third notched specimen formed of a third polymer composition and having substantially equal original structural dimensions as the first and second notched specimens and, when loaded in tension, the third notched specimen undergoes a brittle fracture;
providing a third pipe formed of the third polymer composition and having substantially equal original structural dimensions as the first and second pipes;
conducting the modified Charpy test on the third notched specimen to determine a ductile-to-brittle transition temperature ($T_{db}$) for the third notched specimen;
conducting the S4 test on the third pipe according to ISO 13477 to determine a critical temperature ($T_c$) for the third pipe; and
generating a correlation curve between the ductile-to-brittle temperatures ($T_{db}$) of all the notched specimens and the critical temperatures ($T_c$) of all the pipes.

5. The process according to claim 4, wherein providing the third notched specimen comprises:
forming the third notched specimen from a compression molded plaque of the third polymer composition.

6. A process for predicting a S4 critical temperature of a pipe, the process comprising:
providing a notched test specimen formed of a test polymer composition, wherein the notched test specimen has substantially equal original structural dimensions as the first and second notched specimens and, when loaded in tension, the notched test specimen undergoes a brittle fracture;
conducting a modified Charpy test on the notched test specimen to determine a ductile-to-brittle transition temperature ($T_{db}$) for the notched test specimen;
calculating a predicted S4 critical temperature ($T_c$) from the ductile-to-brittle temperatures ($T_{db}$) based on the correlation curve according to claim 4.

7. The process according to claim 6, wherein providing the notched test specimen comprises:
forming the notched test specimen from a compression molded plaque of the test polymer composition.

8. The process according to claim 6, wherein the first, second, and third notched specimens and the notched test specimen each has a thickness defined by:

$$B \geq 2.5 * \left(\frac{K_{IC}}{\sigma_y}\right)^2$$

wherein:
B(m) is the thickness of the notched specimen
$K_{IC}$(Pa·m$^{1/2}$) is the fracture toughness of the notched specimen; and
$\sigma_y$(Pa·m$^{-1}$) is the yield stress of the notched specimen.

9. The process according to claim 6, wherein the first, second, and third notched specimens and the notched test specimen each has a thickness less than 20 mm.

10. The process according to claim 6, the first, second, and third notched specimens and the notched test specimen each has a thickness less than 10 mm.

11. The process according to claim 6, wherein the first, second, and third polymer compositions and the test polymer composition each is derived from a sample coupon from molded end use articles, polymer fluff, or pellets.

12. The process according to claim 4, wherein the first, second and third pipes each has a standard dimension ratio of about 7 to about 21, wherein the standard dimension ratio is a ratio of an outer pipe diameter to a pipe wall thickness.

13. The process according to claim 4, wherein the first, second and third pipes each has a standard dimension ratio of about 9 to about 17, wherein the standard dimension ratio is a ratio of an outer pipe diameter to a pipe wall thickness.

14. The process according to claim 4, wherein the first, second and third pipes each has a standard dimension ratio of about 11, wherein the standard dimension ratio is a ratio of an outer pipe diameter to a pipe wall thickness.

15. The process according to claim 4, wherein the first, second and third pipes each has a nominal outer diameter of about 2 to about 16 inches.

16. The process according to claim 4, wherein the first, second and third pipes each has a nominal outer diameter of about 2 to about 8 inches.

17. The process according to claim 4, wherein the ductile-to-brittle transition temperature ($T_{db}$) for each of the first, second and third notched specimens is from about −80° C. to about −5° C.

18. The process according to claim 4, wherein the ductile-to-brittle transition temperature ($T_{db}$) for each of the first, second and third notched specimens is from about −40° C. to about 5° C.

19. The process according to claim 4, wherein the ductile-to-brittle transition temperature ($T_{db}$) for each of the first, second and third notched specimens is from about −25° C. to about 0° C.

20. The process according to claim 4, wherein the S4 $T_c$ for each of the first, second and third pipes is from about −40° C. to about 25° C.

21. The process according to claim 4, wherein the S4 $T_c$ for each of the first, second and third pipes is from about 0° C. to about 20° C.

22. The process according to claim 4, wherein the first, second, and third polymer compositions and the test polymer composition each comprises a polyethylene resin.

23. The process according to claim 4, wherein the first, second, and third polymer compositions and the test polymer composition each comprises a medium-density or a high-density polyethylene.

24. The process according to claim 4, wherein the first, second, and third pipes are each a thermoplastic pipe.

25. The process according to claim 1, wherein the coefficient of determination ($R^2$) is from about 4% to about 52% greater than the comparative coefficient of determination ($R_C^2$).

26. A process for preparing a polyethylene pipe, the process comprising:
generating the correlation curve between ductile-to-brittle temperatures ($T_{db}$) and critical temperatures ($T_c$) according to claim 1;
providing a test specimen formed of a test polyethylene composition, wherein the test specimen is notched and has substantially equal original structural dimensions as the first and second notched specimens and, when loaded in tension, the test specimen undergoes a brittle fracture;
conducting a modified Charpy test on the test specimen to determine a ductile-to-brittle transition temperature ($T_{db}$) for the test specimen;
calculating a predicted S4 critical temperature ($T_c$) of a pipe formed of the test polyethylene composition based on the correlation curve;
adjusting the test polyethylene composition to obtain a new polyethylene composition having a desired S4 critical temperature ($T_c$) based on the correlation curve; and
melting the new polyethylene composition and forming the molten polyethylene composition into pipe.

27. A process for preparing a polyethylene pipe according to claim 26, wherein adjusting the test polyethylene composition comprises or is selected from altering [1] the percentage comonomer in the test polyethylene composition, [2] the polydispersity index of the test polyethylene composition, [3] the molecular weight distribution of the test polyethylene composition, [4] the identity of the comonomer(s) in the test polyethylene composition, [5] the relative proportion of constituent polymers in the test polyethylene composition when it is multimodal, and [6] any combination thereof.

28. A process for preparing a polyethylene pipe according to claim 26, wherein the new polyethylene composition is a multimodal medium-density polyethylene has a density of from about 0.925 g/ml to about 0.942 g/ml.

29. A process for preparing a polyethylene pipe according to claim 26, wherein the new polyethylene composition is a multimodal medium-density polyethylene has a density of from about 0.928 g/ml to about 0.940 g/ml.

30. A process for preparing a polyethylene pipe according to claim 29, wherein the new polyethylene composition is a bimodal polyethylene.

31. A process for preparing a polyethylene pipe according to claim 26, wherein the new polyethylene composition has a PENT value of from about 500 hours to about 20,000 hours as measured by ASTM F1473.

32. A process for preparing a polyethylene pipe according to claim 26, wherein the new polyethylene composition has a Charpy impact energy of from about 1.0 J to about 3.0 J.

33. A process for preparing a polyethylene pipe according to claim 26, wherein the new polyethylene composition has a flexural modulus, 2% secant of from about 80 kpsi to about 110 kpsi.

34. A process for preparing a polyethylene pipe according to claim 26, wherein the new polyethylene composition has an elongation at break of greater than about 450%.

35. A process for preparing a polyethylene pipe according to claim 26, wherein the new polyethylene composition has a Young's modulus of from about 120 kpsi to about 190 kpsi.

36. A process for preparing a polyethylene pipe according to claim 26, wherein the new polyethylene composition has a tensile strength at yield of from about 2600 psi to less than about 3,000 psi.

37. A pipe made according to the process of claim 26.

* * * * *